US012691222B2

(12) United States Patent
Lee et al.

(10) Patent No.: US 12,691,222 B2
(45) Date of Patent: Jul. 28, 2026

(54) TECHNIQUES FOR DETERMINING MEDICATION CORRECTION FACTORS IN AUTOMATIC MEDICATION DELIVERY SYSTEMS

(71) Applicant: INSULET CORPORATION, Acton, MA (US)

(72) Inventors: Joon Bok Lee, Acton, MA (US); James Graham, Tyngsboro, MA (US); Jason O'Connor, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 639 days.

(21) Appl. No.: 18/164,669

(22) Filed: Feb. 6, 2023

(65) Prior Publication Data

US 2023/0248909 A1    Aug. 10, 2023

Related U.S. Application Data

(60) Provisional application No. 63/307,283, filed on Feb. 7, 2022.

(51) Int. Cl.
A61M 5/172        (2006.01)
G16H 20/17        (2018.01)

(52) U.S. Cl.
CPC .......... A61M 5/1723 (2013.01); G16H 20/17 (2018.01); A61M 2202/0486 (2013.01); A61M 2205/52 (2013.01)

(58) Field of Classification Search
None
See application file for complete search history.

(56) References Cited

U.S. PATENT DOCUMENTS 303,013 A    8/1884  Horton
2,797,149 A    6/1957  Skeggs
(Continued)

FOREIGN PATENT DOCUMENTS

AU    2015200834 A1    3/2015
AU    2015301146 A1    3/2017
(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — Goodwin Procter LLP

(57)        ABSTRACT

Disclosed are processes and techniques for a correction factor determination process for determining a correction factor for delivering a drug to a patient via a drug delivery device. For example, for an insulin delivery device, the disclosed techniques enable adjustment of the patient's correction factor in real time based on the deviation of the patient's glucose concentrations against clinically recommended targets. For example, a method for determining a correction factor may include determining an insulin action ($I_{action}$) for a patient over a duration, the insulin action representing a total insulin metabolized, determining glucose information for the patient over the duration, the glucose information representing glucose activity, and determining an estimated correction factor ($CF_{est}$) based on (glucose information)/(insulin action) for the duration. Other embodiments are described.

18 Claims, 9 Drawing Sheets

(56)  References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |

(56) References Cited

U.S. PATENT DOCUMENTS

| | | | |
|---|---|---|---|
| 6,379,301 B1 * | 4/2002 | Worthington | A61B 5/7275 |
| | | | 128/920 |
| 6,402,689 B1 | 6/2002 | Scarantino et al. | |
| 6,470,279 B1 | 10/2002 | Samsoondar | |
| 6,475,196 B1 | 11/2002 | Vachon | |
| 6,477,901 B1 | 11/2002 | Tadigadapa et al. | |
| 6,484,044 B1 | 11/2002 | Lilienfeld-Toal | |
| 6,491,656 B1 | 12/2002 | Morris | |
| 6,512,937 B2 | 1/2003 | Blank et al. | |
| 6,525,509 B1 | 2/2003 | Petersson et al. | |
| 6,528,809 B1 | 3/2003 | Thomas et al. | |
| 6,540,672 B1 | 4/2003 | Simonsen et al. | |
| 6,544,212 B2 | 4/2003 | Galley et al. | |
| 6,546,268 B1 | 4/2003 | Ishikawa et al. | |
| 6,546,269 B1 | 4/2003 | Kurnik | |
| 6,553,841 B1 | 4/2003 | Blouch | |
| 6,554,798 B1 | 4/2003 | Mann et al. | |
| 6,556,850 B1 | 4/2003 | Braig et al. | |
| 6,558,351 B1 | 5/2003 | Steil et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,562,014 B2 | 5/2003 | Lin et al. | |
| 6,569,125 B2 | 5/2003 | Jepson et al. | |
| 6,572,542 B1 | 6/2003 | Houben et al. | |
| 6,572,545 B2 | 6/2003 | Knobbe et al. | |
| 6,574,490 B2 | 6/2003 | Abbink et al. | |
| 6,575,905 B2 | 6/2003 | Knobbe et al. | |
| 6,580,934 B1 | 6/2003 | Braig et al. | |
| 6,618,603 B2 | 9/2003 | Varalli et al. | |
| 6,633,772 B2 | 10/2003 | Ford et al. | |
| 6,645,142 B2 | 11/2003 | Braig et al. | |
| 6,653,091 B1 | 11/2003 | Dunn et al. | |
| 6,662,030 B2 | 12/2003 | Khalil et al. | |
| 6,669,663 B1 | 12/2003 | Thompson | |
| 6,678,542 B2 | 1/2004 | Braig et al. | |
| 6,699,221 B2 | 3/2004 | Vaillancourt | |
| 6,718,189 B2 | 4/2004 | Rohrscheib et al. | |
| 6,721,582 B2 | 4/2004 | Trepagnier et al. | |
| 6,728,560 B2 | 4/2004 | Kollias et al. | |
| 6,740,059 B2 | 5/2004 | Flaherty | |
| 6,740,072 B2 | 5/2004 | Starkweather et al. | |
| 6,751,490 B2 | 6/2004 | Esenaliev et al. | |
| 6,758,835 B2 | 7/2004 | Close et al. | |
| 6,780,156 B2 | 8/2004 | Haueter et al. | |
| 6,810,290 B2 | 10/2004 | Lebel et al. | |
| 6,837,858 B2 | 1/2005 | Cunningham et al. | |
| 6,837,988 B2 | 1/2005 | Leong et al. | |
| 6,846,288 B2 | 1/2005 | Nagar et al. | |
| 6,862,534 B2 | 3/2005 | Sterling et al. | |
| 6,865,408 B1 | 3/2005 | Abbink et al. | |
| 6,890,291 B2 | 5/2005 | Robinson et al. | |
| 6,936,029 B2 | 8/2005 | Mann et al. | |
| 6,949,081 B1 | 9/2005 | Chance | |
| 6,958,809 B2 | 10/2005 | Sterling et al. | |
| 6,989,891 B2 | 1/2006 | Braig et al. | |
| 6,990,366 B2 | 1/2006 | Say et al. | |
| 7,008,404 B2 | 3/2006 | Nakajima | |
| 7,009,180 B2 | 3/2006 | Sterling et al. | |
| 7,016,713 B2 | 3/2006 | Gardner et al. | |
| 7,018,360 B2 | 3/2006 | Flaherty et al. | |
| 7,025,743 B2 | 4/2006 | Mann et al. | |
| 7,025,744 B2 | 4/2006 | Utterberg et al. | |
| 7,027,848 B2 | 4/2006 | Robinson et al. | |
| 7,043,288 B2 | 5/2006 | Davis, III et al. | |
| 7,060,059 B2 | 6/2006 | Keith et al. | |
| 7,061,593 B2 | 6/2006 | Braig et al. | |
| 7,096,124 B2 | 8/2006 | Sterling et al. | |
| 7,115,205 B2 | 10/2006 | Robinson et al. | |
| 7,128,727 B2 | 10/2006 | Flaherty et al. | |
| 7,139,593 B2 | 11/2006 | Kavak et al. | |
| 7,139,598 B2 | 11/2006 | Hull et al. | |
| 7,144,384 B2 | 12/2006 | Gorman et al. | |
| 7,171,252 B1 | 1/2007 | Scarantino et al. | |
| 7,190,988 B2 | 3/2007 | Say et al. | |
| 7,204,823 B2 | 4/2007 | Estes et al. | |
| 7,248,912 B2 | 7/2007 | Gough et al. | |
| 7,267,665 B2 | 9/2007 | Steil et al. | |
| 7,271,912 B2 | 9/2007 | Sterling et al. | |
| 7,278,983 B2 | 10/2007 | Ireland et al. | |
| 7,291,107 B2 | 11/2007 | Hellwig et al. | |
| 7,291,497 B2 | 11/2007 | Holmes et al. | |
| 7,303,549 B2 | 12/2007 | Flaherty et al. | |
| 7,303,622 B2 | 12/2007 | Loch et al. | |
| 7,303,922 B2 | 12/2007 | Jeng et al. | |
| 7,354,420 B2 | 4/2008 | Steil et al. | |
| 7,388,202 B2 | 6/2008 | Sterling et al. | |
| 7,402,153 B2 | 7/2008 | Steil et al. | |
| 7,404,796 B2 | 7/2008 | Ginsberg | |
| 7,429,255 B2 | 9/2008 | Thompson | |
| 7,460,130 B2 | 12/2008 | Salganicoff | |
| 7,481,787 B2 | 1/2009 | Gable et al. | |
| 7,491,187 B2 | 2/2009 | Van Den Berghe et al. | |
| 7,500,949 B2 | 3/2009 | Gottlieb et al. | |
| 7,509,156 B2 | 3/2009 | Flanders | |
| 7,547,281 B2 | 6/2009 | Hayes et al. | |
| 7,569,030 B2 | 8/2009 | Lebel et al. | |
| 7,608,042 B2 | 10/2009 | Goldberger et al. | |
| 7,651,845 B2 | 1/2010 | Doyle, III et al. | |
| 7,680,529 B2 | 3/2010 | Kroll | |
| 7,734,323 B2 | 6/2010 | Blomquist et al. | |
| 7,766,829 B2 | 8/2010 | Sloan et al. | |
| 7,785,258 B2 | 8/2010 | Braig et al. | |
| 7,806,854 B2 | 10/2010 | Damiano et al. | |
| 7,806,886 B2 | 10/2010 | Kanderian, Jr. et al. | |
| 7,918,825 B2 | 4/2011 | OConnor et al. | |
| 7,946,985 B2 | 5/2011 | Mastrototaro et al. | |
| 7,972,296 B2 | 7/2011 | Braig et al. | |
| 8,221,345 B2 | 7/2012 | Blomquist | |
| 8,251,907 B2 | 8/2012 | Sterling et al. | |
| 8,449,524 B2 | 5/2013 | Braig et al. | |
| 8,452,359 B2 | 5/2013 | Rebec et al. | |
| 8,454,576 B2 | 6/2013 | Mastrototaro et al. | |
| 8,467,980 B2 | 6/2013 | Campbell et al. | |
| 8,478,557 B2 | 7/2013 | Hayter et al. | |
| 8,547,239 B2 | 10/2013 | Peatfield et al. | |
| 8,597,274 B2 | 12/2013 | Sloan et al. | |
| 8,622,988 B2 | 1/2014 | Hayter | |
| 8,810,394 B2 | 8/2014 | Kalpin | |
| 9,061,097 B2 | 6/2015 | Holt et al. | |
| 9,171,343 B1 | 10/2015 | Fischell et al. | |
| 9,233,204 B2 | 1/2016 | Booth et al. | |
| 9,486,571 B2 | 11/2016 | Rosinko | |
| 9,579,456 B2 | 2/2017 | Budiman et al. | |
| 9,743,224 B2 | 8/2017 | San Vicente et al. | |
| 9,907,515 B2 | 3/2018 | Doyle, III et al. | |
| 9,980,140 B1 | 5/2018 | Spencer et al. | |
| 9,984,773 B2 | 5/2018 | Gondhalekar et al. | |
| 10,248,839 B2 | 4/2019 | Levy et al. | |
| 10,335,464 B1 | 7/2019 | Michelich et al. | |
| 10,583,250 B2 | 3/2020 | Mazlish et al. | |
| 10,737,024 B2 | 8/2020 | Schmid | |
| 10,987,468 B2 | 4/2021 | Mazlish et al. | |
| 11,197,964 B2 | 12/2021 | Sjolund et al. | |
| 11,260,169 B2 | 3/2022 | Estes | |
| 2001/0021803 A1 | 9/2001 | Blank et al. | |
| 2001/0034023 A1 | 10/2001 | Stanton, Jr. et al. | |
| 2001/0034502 A1 | 10/2001 | Moberg et al. | |
| 2001/0051377 A1 | 12/2001 | Hammer et al. | |
| 2001/0053895 A1 | 12/2001 | Vaillancourt | |
| 2002/0010401 A1 | 1/2002 | Bushmakin et al. | |
| 2002/0010423 A1 | 1/2002 | Gross et al. | |
| 2002/0016568 A1 | 2/2002 | Lebel et al. | |
| 2002/0040208 A1 | 4/2002 | Flaherty et al. | |
| 2002/0123740 A1 | 9/2002 | Flaherty et al. | |
| 2002/0128543 A1 | 9/2002 | Leonhardt | |
| 2002/0147423 A1 | 10/2002 | Burbank et al. | |
| 2002/0155425 A1 | 10/2002 | Han et al. | |
| 2002/0161288 A1 | 10/2002 | Shin et al. | |
| 2003/0023148 A1 | 1/2003 | Lorenz et al. | |
| 2003/0050621 A1 | 3/2003 | Lebel et al. | |
| 2003/0060692 A1 | 3/2003 | L. Ruchti et al. | |
| 2003/0086074 A1 | 5/2003 | Braig et al. | |
| 2003/0086075 A1 | 5/2003 | Braig et al. | |

(56) References Cited

U.S. PATENT DOCUMENTS

| | | |
|---|---|---|
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |

(56)  References Cited

U.S. PATENT DOCUMENTS

| | | |
|---|---|---|
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0001002 A1* | 1/2016 | Yodfat ................ A61M 5/1408 |
| | | 604/152 |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |

| | | |
|---|---|---|
| 2016/0082188 A1* | 3/2016 | Blomquist ................ A61P 3/10 |
| | | 604/66 |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2021/0244880 A1* | 8/2021 | Lee ..................... A61M 5/1723 |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2007 |

(56) References Cited

FOREIGN PATENT DOCUMENTS

| | | | |
|---|---|---|---|
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 200032258 A1 | 6/2000 |
| WO | 0172354 A2 | 10/2001 |
| WO | 2002015954 A1 | 2/2002 |
| WO | 2002043866 A2 | 6/2002 |
| WO | 2002082990 A1 | 10/2002 |
| WO | 2003016882 A1 | 2/2003 |
| WO | 2003039362 A1 | 5/2003 |
| WO | 2003045233 A1 | 6/2003 |
| WO | 2004043250 A1 | 5/2004 |
| WO | 2005110601 A1 | 5/2004 |
| WO | 2004092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018132750 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The Nice-Sugar (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

International Search Report and Written Opinion in PCT/US2008/079641 dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

(56) References Cited

OTHER PUBLICATIONS

Berger, "An Enhanced Algorithm for Linear Multivariate Calibration," Analytical Chemistry, vol. 70, No. 3, pp. 623-627, Feb. 1, 1998.

Billman et. al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved on Dec. 29, 2010 from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Patent Application No. 21168591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

(56) References Cited

OTHER PUBLICATIONS

International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2023/062013, mailed May 23, 2023, 13 pages.
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/> (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.

* cited by examiner

<u>100</u>

301 — Standardized CGM Metrics for Clinical Care

| | |
|---|---|
| 1. Number of days CGM worn (recommend 14 days) (42,43) | |
| 2. Percentage of time CGM is active (recommend 70% of data from 14 days) (41,42) | |
| 3. Mean glucose | |
| 4. Glucose management indicator (GMI) (75) | |
| 5. Glycemic variability (%CV) target ≤36% (90)* | |
| 6. Time above range(TAR): % of readings and time >250 mg/dL (>13.9 mmol/L) | Level 2 |
| 7. Time above range(TAR): % of readings and time 181-250 mg/dL (10.1-13.9 mmol/L) | Level 1 |
| 8. Time in range (TIR): % of readings and time 70-180 mg/dL (3.9-10.0 mmol/L) | In range |
| 9. Time below range (TBR): % of readings and time 54-69 mg/dL (3.0-3.8 mmol/L) | Level 1 |
| 10. Time below range (TBR): % of readings and time <54 mg/dL (<3.0 mmol/L) | Level 2 |

311 — Target Guidance for Glycemic Control in T1D and T2D Patients

| Diabetes group | TIR | | TBR | | TAR | |
|---|---|---|---|---|---|---|
| | Target range | % of readings; time per day | Below target level | % of readings; time per day | Above target level | % of readings; time per day |
| Type 1*/ type 2 | 70-180 mg/dL (3.9-10.0 mmol/L) | >70%; >16 h, 48 min | <70 mg/dL (<3.9 mmol/L) <54 mg/dL (<3.0 mmol/L) | <4%; <1 h <1%; <15 min | >180 mg/dL (>10.0 mmol/L) >250 mg/dL (>13.9 mmol/L) | <25%; <6 h <5%; <1 h, 12 min |
| Older/high-risk# type 1/type 2 | 70-180 mg/dL (3.9-10 mmol/L) | >50%; >12 h | <70 mg/dL (<3.9 mmol/L) | <1%; <15 min | >250 mg/dL (>13.9 mmol/L) | <10%; <2 h, 24 min |

OBTAIN PATIENT GLUCOSE LEVEL
_502_

DETERMINE TARGET GLUCOSE DIFFERENCE BASED ON
A DIFFERENCE BETWEEN PATIENT GLUCOSE LEVEL
AND TARGET GLUCOSE LEVEL
_504_

DETERMINE DOSAGE BASED ON TARGET GLUCOSE
DIFFERENCE
_506_

DELIVER DRUG TO PATIENT BASED ON TARGET
GLUCOSE DIFFERENCE
_512_

*600*

RECEIVE PATIENT INFORMATION FOR CYCLE DURATION
*602*

DETERMINE INSULIN ACTION
*604*

DETERMINE MEAL FACTOR
*606*

DETERMINE GLUCOSE MEAL FACTOR
*608*

DETERMINE GLUCOSE ACTION
*610*

DETERMINE CORRECTION FACTOR BASED ON INSULIN
ACTION AND GLUCOSE ACTION
*612*

DELIVER DRUG TO PATIENT USING CORRECTION
FACTOR
*614*

*700*

RECEIVE PATIENT INFORMATION FOR CYCLE DURATION
*702*

DETERMINE INSULIN ABSORBED
*704*

DETERMINE ABSORBED CARBOHYDRATES
*706*

DETERMINE GLUCOSE RISE DUE TO ABSORBED
CARBOHYDRATES
*708*

DETERMINE NET GLUOSE CHANGE
*710*

DETERMINE ESTIMATED CORRECTION FACTOR
*712*

DELIVER DRUG TO PATIENT USING CORRECTION
FACTOR
*714*

TECHNIQUES FOR DETERMINING MEDICATION CORRECTION FACTORS IN AUTOMATIC MEDICATION DELIVERY SYSTEMS

RELATED APPLICATIONS

This application claims the benefit of U.S. Provisional Patent Application No. 63/307,283, filed Feb. 7, 2022, the contents of which are incorporated herein by reference in their entirety.

BACKGROUND

Automated drug delivery systems may operate to provide dosages of a drug based on patient characteristics. For example, an automated drug delivery system may monitor an analyte of the patient and infuse the patient with a dosage of the drug to maintain the analyte within a target value or range. An automated insulin delivery (AID) system, for instance, may include a closed control loop system that operates to keep a patient blood glucose level close to a target blood glucose level. In a typical AID system, a controller receives a current blood glucose level reading and compares the current blood glucose level to the target blood glucose level and adjusts the basal insulin delivery in an attempt to reduce the difference between the target blood glucose level and the current blood glucose level.

Although automated drug delivery systems, such as an AID system, are able to dynamically adjust for variations in the analyte concentration, conventional systems generally become deterministic or semi-deterministic and deliver a same or similar dosage of the drug for different analyte value inputs even if the analyte concentration should require a different dosage. For example, existing systems are generally deficient at adjusting dosage parameters based on patient insulin and/or glucose activity, such as dosage correction, insulin decay, or sensitivity factors. Accordingly, conventional automated drug delivery devices are not able to adequately and efficiently provide dynamic adjustment of drug dosages based on patient activity patterns.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one embodiment, a controller for operating an insulin delivery device may include a processor and a memory storing instructions that, when executed by the processor, may operate the controller to determine an insulin action ($I_{action}$) for a patient over a duration, the insulin action representing a total insulin metabolized; determine glucose information for the patient over the duration, the glucose information representing glucose activity; and determine an estimated correction factor ($CF_{est}$) based on (glucose information)/(insulin action) for the duration.

In some embodiments of the controller, $I_{action}$ may be determined based on an insulin decay curve for the duration. In various embodiments of the controller, $I_{action}$ may be determined using the following:

$$I_{action}(i) = \left(\sum\nolimits_{k=1}^{n} I(i-k)\right) - IOB(i),$$

where n is determined based on (duration)/(duration increments).

In some embodiments of the controller, the glucose information may include a glucose action ($G_{action}$) value. In various embodiments of the controller, $G_{action}$ may be determined using the following:

$$G_{action}(i) = \frac{1}{48}\sum\nolimits_{k=1}^{48}(G(i-k)-x),$$

where x is a target glucose value.

In some embodiments of the controller, the glucose information may include a glucose meal excursion value ($G_{meal}$). In various embodiments of the controller, $G_{meal}$ value may be determined using the following:

$$G_{meal}(i) = \left(\sum\nolimits_{k=1}^{48} CHO(i-k) - COB(i)\right) \cdot M_f,$$

where CHO is all carbohydrates ingested, COB is carbohydrates-on-board, and $M_f$ is a meal factor.

In some embodiments of the controller, the instructions, when executed by the processor, may operate the controller to determine a final correction factor ($CF_{final}$) based on $CF_{est}$ using the following:

$$CF_{final}(i) = 0.8 \cdot \frac{1800}{\sum\nolimits_{k=1}^{244} I(i-k)} + 0.2 \cdot CF_{est}(i).$$

In exemplary embodiments of the controller, the duration may include about 4 hours.

In one embodiment, a method for operating a drug delivery device may include, via a processor of a controller determining an insulin action ($I_{action}$) for a patient over a duration, the insulin action representing a total insulin metabolized, determining glucose information for the patient over the duration, the glucose information representing glucose activity, and determining an estimated correction factor ($CF_{est}$) based on (glucose information)/(insulin action) for the duration.

In some embodiments of the method, $I_{action}$ may be determined based on an insulin decay curve for the duration. In various embodiments of the method, $I_{action}$ may be determined using the following:

$$I_{action}(i) = \left(\sum\nolimits_{k=1}^{n} I(i-k)\right) - IOB(i),$$

where n is determined based on (duration)/(duration increments).

In some embodiments of the method, the glucose information may include a glucose action ($G_{action}$) value. In various embodiments of the method, $G_{action}$ may be determined using the following:

$$G_{action}(i) = \frac{1}{48}\sum\nolimits_{k=1}^{48}(G(i-k)-x),$$

where x is a target glucose value.

In exemplary embodiments of the method, the glucose information may include a glucose meal excursion value $(G_{meal})$. In some embodiments of the method, $G_{meal}$ value may be determined using the following:

$$G_{meal}(i) = \left(\sum_{k=1}^{48} CHO(i-k) - COB(i)\right) \cdot M_f,$$

where CHO is all carbohydrates ingested, COB is carbohydrates-on-board, and $M_f$ is a meal factor.

In various embodiments of the method, the method may include determining a final correction factor ($CF_{final}$) based on $CF_{est}$ using the following:

$$CF_{final}(i) = 0.8 \cdot \frac{1800}{\sum_{k=1}^{244} I(i-k)} + 0.2 \cdot CF_{est}(i).$$

In some embodiments of the method, the duration may be about 4 hours.

BRIEF DESCRIPTION OF THE DRAWINGS

FIGS. 3A and 3B illustrate examples of standardized glucose control metrics in accordance with the present disclosure;

Figure 1:
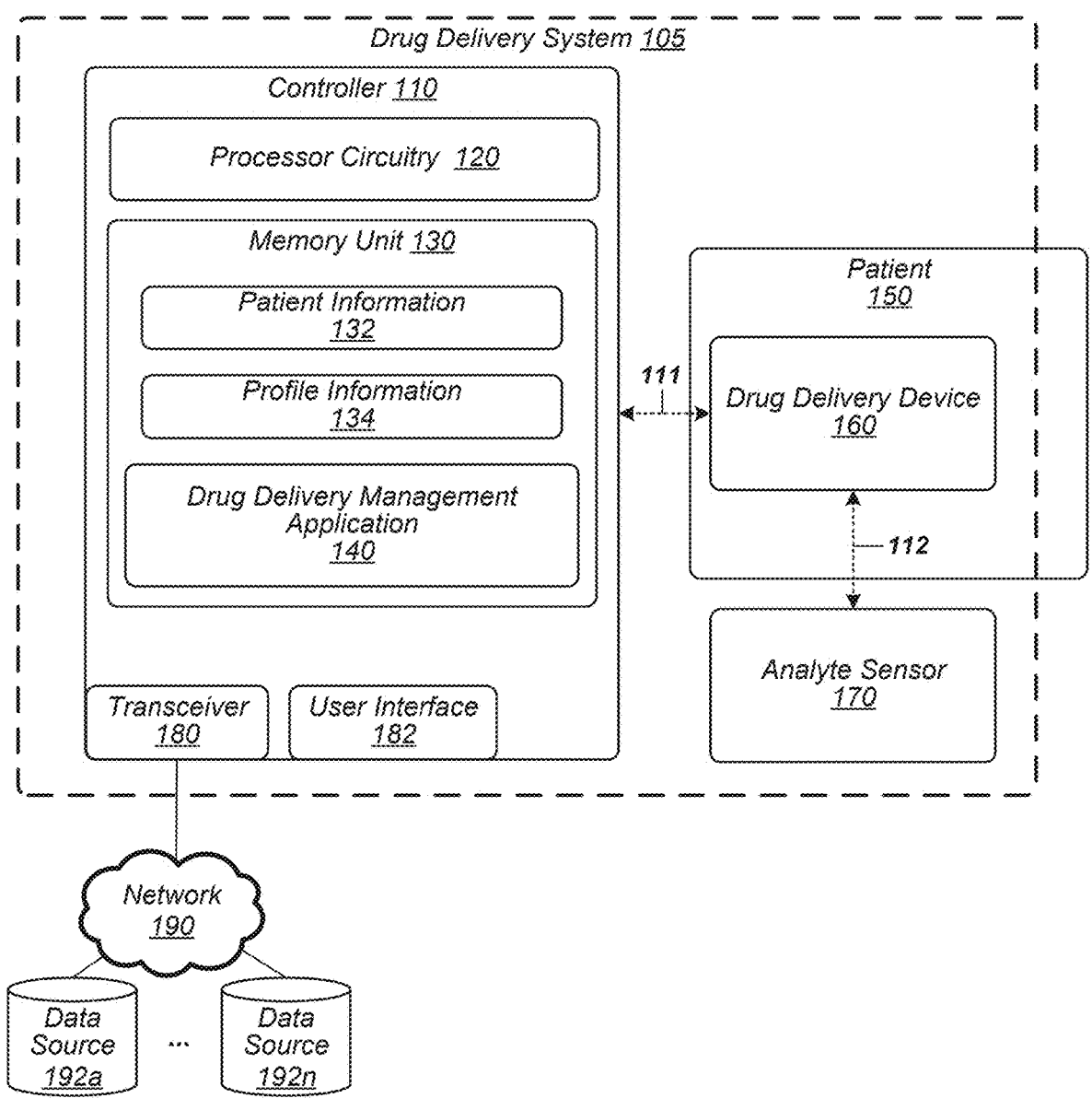
FIG. 1 illustrates a first exemplary embodiment of an operating environment in accordance with the present disclosure.

The drawings are not necessarily to scale. The drawings are merely representations, not intended to portray specific parameters of the disclosure. The drawings are intended to depict example embodiments of the disclosure, and therefore should not be considered as limiting in scope. In the drawings, like numbering represents like elements.

DETAILED DESCRIPTION

Various features of drug delivery devices and processes will now be described more fully hereinafter with reference to the accompanying drawings, in which one or more features of the drug delivery devices and processes will be shown and described. It should be appreciated that the various features or the like described hereinafter may be used independently of, or in combination, with each other. It will be appreciated that a drug delivery device and/or process for operating a drug delivery device disclosed herein may be embodied in many different forms and should not be construed as being limited to the embodiments set forth herein. Rather, these embodiments are provided so that this disclosure will convey certain or features of the drug delivery device and/or process for operating the drug delivery device to those skilled in the art.

Disclosed herein are drug delivery devices and processes for operating drug delivery devices. In some embodiments, a drug delivery process may include a correction factor determination process for determining a drug sensitivity or correction factor for controlling a concentration of an analyte in the body of the patient. In one example, the drug may be or may include insulin and the analyte may be or may include glucose.

In general, a correction factor may represent an effect on an analyte based on a unit of a drug. For example, for insulin-based glucose control, the correction factor may represent the amount of a drop in blood glucose (or "blood sugar") for one unit of insulin. In one example, the correction factor may be used manually by a patient and/or automatically by an automated insulin delivery (AID) device to deliver an amount of insulin, such as a bolus infusion of insulin required for a high blood glucose reading and/or a reduction in a meal bolus for a low blood glucose reading. In another example, the correction factor may be used to determine an amount of carbohydrates that should be consumed by a patient to increase a low blood glucose level to a target blood glucose level.

Each patient has an individual correction factor that is best for their particular condition. This correction factor may change over time for the individual. The correction factor is an important parameter for determining proper insulin dosage: if the correction factor is too high, then the blood glucose may not actually be dropping as much as estimated and could lead to high blood glucose levels; alternatively, if the correction factor is too low, a correction bolus may provide too much insulin and result in a low blood glucose level.

In some examples, the correction factor may be determined based on the total daily dosage (TDD) of insulin as well as other factors, such as patient age, weight, activity level, insulin decay rate, carbohydrate ingestion, and/or the like. In one example, the correction factor may be based on an insulin sensitivity factor, such as the "1800 rule," the "1500 rule," and/or the like. For instance, if a patient has a TDD of 50 units, then the correction factor has traditionally been determined as 1800/50=36 for the 1800 rule.

However, an accurate determination of a correction factor using conventional methods is typically inaccurate because the calculation lacks sufficient information, such as properly accounting for carbohydrate ingestion, and does not adequately detect changes in insulin sensitivity throughout the day and/or during different periods of activity. Conventional methods often measure for insulin sensitivity during fasting periods, such as at night and/or during sleep periods when no food (i.e., carbohydrates) are being consumed. Existing processes are not able to adequately estimate or otherwise determine a patient correction factor due to meal interference when the patient is not fasting and/or during different levels of activity (e.g., exercise, and/or the like). In addition, a patient's correction factor may change over time, for instance, as they experience prolonged exposure to insulin, age, add/remove other medications, change their diet, and/or the like. Furthermore, patients who manually calculate their correction factors have difficulty assessing exactly how much their insulin sensitivities may change over time, and manually changing these parameters is prone to error and incurs additional burden in their daily diabetes care (which reduces consistent adoption of this approach by patients).

Accordingly, some embodiments may provide a drug delivery process that automatically determines a correction factor for a patient. In various embodiments, the correction factor may be determined in real-time, substantially real-time, and/or at discrete intervals (for instance, every five minutes, every four hours, every 24 hours, and/or the like).

In one embodiment, for example, a drug delivery process may include a correction factor determination process to adjust a patient's correction factor (in real-time, substantially real-time, and/or at discrete intervals) based on a deviation of the user's glucose concentrations compared against glucose concentration targets, such as clinically recommended targets for glucose control.

As described below, a drug delivery system may include a number of components, such as a drug delivery device, a controller, and an analyte sensor. The drug delivery device may be controlled and operate based on signals containing information received from the analyte sensor. Control may be based on an application executing on the drug delivery device, the controller, the analyte sensor, or may be distributed between two or more of the drug delivery device, the controller, or the analyte sensor. For example, the drug delivery device may be configured to deliver a drug at a dosage or frequency based on a measured analyte concentration associated with a patient.

An example of an automatic analyte control application or logic circuit may be specific to a particular type of analyte. Non-limiting examples of analytes may include blood glucose, a hormone, a protein, a medication, ketone, alcohol level, and the like. A control application specific to controlling a patient's blood glucose may be an Automatic Glucose Control (AGC) application that may rely on a blood glucose measurement value and other information that may be provided by a continuous glucose monitor (CGM). "Automatic glucose control" may refer to an algorithm or computer application that is operable to use blood glucose measurements to determine amounts of a drug to be delivered to a user in order to maintain the user's measured blood glucose within a set range of blood glucose measurement values. "Blood glucose measurement value" may refer to a numerical value representative of an amount of glucose in a user's blood that has the units of milligrams per deciliter (mg/dL). The other information provided by the CGM may be included as part of, or separately from, the blood glucose measurement value. The AGC may be operable to estimate and store the estimated values of CGM based upon various parameters within the drug delivery system. Such future trend information may be useful in case of missing CGM values to estimate suggested insulin for a short duration.

Although insulin delivery devices, insulin, blood glucose, AGC applications, and CGM devices are used in examples in the present disclosure, embodiments are not so limited as these are provided for illustrative purposes. Embodiments may operate with various types of fluid or drug delivery devices, drugs or other fluids, analytes, automated drug delivery applications, and/or analyte sensors in accordance with the teachings of the present disclosure.

Therefore, drug delivery systems and methods for operating drug delivery devices according to some embodiments may provide multiple technological advantages over conventional systems and methods. In one non-limiting technological advantage, systems may be configured to provide a drug based on a dynamically determined correction factor calculated in real-time, substantially real-time, and/or at discrete intervals. For example, some embodiments may include an AID configured to dynamically determine an insulin correction factor and to provide insulin to a patient based, at least in part, on the correction factor. In another non-limiting technological advantage, drug delivery processes according to some embodiments may be able to determine a correction factor that is more accurate than correction factors determined using conventional automatic and/or manual methods because, inter alia, the correction factor determination accounts for non-fasting conditions, such as meal or carbohydrate ingestion, activity levels, and/or other factors.

The non-limiting technological advantages may include improvements in computing technology and/or a technical field. For instance, systems and methods according to some embodiments may improve conventional logic devices, controllers, computing devices, and/or other computing technology for controlling drug delivery systems by providing computing technology capable of analyte-based drug delivery control based on accurate, dynamically-calculated correction factors. In addition, systems and methods according to some embodiments may improve the field of automated drug delivery, including, for example, wearable insulin drug delivery devices and associated processes for controlling these devices, drug therapy, diabetes therapy, and/or the like. Furthermore, the methods according to some embodiments may be applied to the practical applications of controlling a drug delivery device, providing a dosage of a drug to a patient, drug therapy, and/or diabetes therapy. Embodiments are not limited in this context. Additional technological advantages, practical applications, and improvements to computing technology and/or technical fields would be known to a person of skill in the art in view of the teachings of the present disclosure.

FIG. 1 illustrates features of the subject matter in accordance with an embodiment of a drug delivery system 105 of an operating environment 100. "Drug delivery system" may refer to a drug delivery device and an analyte sensor, such as a continuous glucose monitor (CGM), and, in some configurations, a controller. "Drug delivery device" may refer to a device configured to administer a liquid drug to a user. A drug delivery device may be the same or substantially similar to the OmniPod® device or system provided by Insulet Corporation of Acton, Massachusetts, United States, for example, as described in U.S. Pat. Nos. 7,303,549; 7,137,964; and/or 6,740,059, each of which is incorporated herein by reference in its entirety.

The drug delivery device may respond to command signals received from a controller, which may be a separate device. Alternatively, the drug delivery device may be configured with a processor that is not separate from the drug delivery device but is operable to perform functions the same as a remote controller. "Controller" may refer to processor or a device having a processor that is configured to control operation of a drug delivery device and transmit and receive information related to measured blood glucose of a user associated with the drug delivery device and the controller. The functions performed by the controller may be executed by a processor integral to the drug delivery device. "Continuous glucose monitor" (CGM) may refer to a wearable device that may at least include a sensor configured to measure the blood glucose of a wearer, a transmitter to transmit blood glucose measurement values measured by the sensor, and logic circuitry that controls the sensor and the transmitter.

Drug delivery system 105 may include a logic device or controller 110, drug delivery device 160, and an analyte sensor 170. Controller 110 may communicate with drug delivery device 160 via communication link 111 and drug delivery device 160 may communicate with the analyte sensor 170 via a communication link 112. "Communication link" may refer to a signal pathway between a first device and a second device. As described below, information may be exchanged between the first device and the second device where both devices may transmit and receive information or other signals.

In some embodiments, controller 110 may be a smart phone or other mobile computing form factor in wired or wireless communication with drug delivery device 160. For example, controller device 110 and drug delivery device 160 may communicate via various wireless protocols, including, without limitation, Wi-Fi (i.e., IEEE 802.11), radio frequency (RF), Bluetooth®, Zigbee™, near field communication (NFC), Medical Implantable Communications Service (MICS), and/or the like. In another example, controller 10 and adjustment compliance device may communicate via various wired protocols, including, without limitation, universal serial bus (USB), Lightning, serial, and/or the like.

Although controller 110 (and components thereof), drug delivery device 160, and analyte sensor 170 are depicted as separate devices, embodiments are not so limited. For example, in some embodiments, controller 110, drug delivery device 160, and/or analyte sensor 170 may be a single device. In another example, some or all of the components of controller 110 may be included in drug delivery device 160. For example, drug delivery device 160 may include processor circuitry 120, memory unit 130, and/or the like. In some embodiments, each of controller 110 and drug delivery device 160 may include a separate processor circuitry 120, memory unit 130, and/or the like capable of facilitating automatic analyte control and/or device initialization processes according to some embodiments, either individually or in operative combination. Embodiments are not limited in this context (see, for example, FIG. 8)

Drug delivery device 160 may include at least one housing and a number of components to facilitate automated delivery of a drug to patient 150. For example, drug delivery device 160 may include a reservoir for storing the drug, a needle and/or cannula for delivering the drug into the body of the patient, and a pump for transferring the drug from the reservoir, through the needle or cannula, and into the body of the patient. In some embodiments, the drug may be or may include insulin, glucagon like peptide (e.g., GLP-1), pramlintide, or a combination thereof. Drug delivery device 160 may also include a power source (not shown), such as a battery, for supplying power to the pump and/or other components of drug delivery device 160. Embodiments are not limited in this context, for example, as drug delivery device 160 may include more or fewer components.

"Analyte sensor" may refer to a sensing and measuring device that may be configured to measure one or more of lactate, ketones, uric acid, sodium, a protein, potassium, alcohol levels, hormone levels, blood glucose, a medication, a drug, a chemotherapy drug, glucagon or a glucagon-like peptide, and/or the like. In some examples, analyte sensor 170 may be configured as a CGM, which may refer to a wearable device that may at least include a sensor configured to measure blood glucose of a wearer, a transmitter to transmit blood glucose measurement values measured by the sensor (for example, to controller 110 and/or drug delivery device 160), and logic circuitry that controls the sensor and the transmitter. Analyte sensor 170 may be configured, with a processor, a communication device, a memory, a sensing/measuring device, and/or other components (see, for example, FIG. 8). Analyte sensor 170 may output analyte measurement values to any devices that are communicatively coupled to analyte sensor 170 when operating properly (e.g., full power supply, established wireless connectivity, sensing/measuring device operation is proper, and whatever other functions enable the analyte sensor to detect and output an analyte measurement value).

In drug delivery system 105 of FIG. 1, analyte sensor 170 and drug delivery device 160 may be communicatively coupled to one another, and controller 110 and drug delivery device 160 may be communicatively coupled to one another. For example, controller 110 may be wirelessly coupled to drug delivery device 160 via communication link 111 and drug delivery device 160 may be wirelessly coupled to analyte sensor 170 via communication link 112. In some embodiments, controller 110 and analyte sensor 170 may be communicatively coupled to one another, for instance, via communications link 113.

Analyte sensor 170 may provide an analyte measurement value at a specific time during an operational time period to drug delivery device 160. An "analyte measurement value" may refer to a numerical value representative of an amount of an analyte being monitored by an analyte sensor and that has the units in common usage of the analyte being monitored, such as milligrams per deciliter (mg/dL), a percentage, or the like. In an example, analyte sensor 170 may be configured to output an analyte measurement value at a predetermined cadence (e.g., every 1, 2, 5, 6, 8 or 10 minutes) or once within a set period of time (e.g., at time=0 in a 5 minute period of time). The set period of time in the example of a diabetes treatment plan may be referred to as a "cycle" or "cycle time," which may last about 5 seconds, about 10 seconds, about 30 seconds, 1 minute, or about 1 minute, 5 minutes, or about 5 minutes, about 3 minutes, or about 10 minutes, or the like. A specific time during the operation may be at the beginning of the operational time period.

The outputted analyte measurement value may be received by a drug delivery management application 140 executing on controller 110 and/or automatic analyte control (AAC) application executing on drug delivery device 160 and/or controller 110, but may be shared with other applications, such as an automated medication delivery application, an artificial pancreas application, and/or the like. The analyte measurement values may include information that includes an analyte measurement value, such a blood glucose measurement value, but also information such as analyte rate of change, status information related to a sensing/measuring device in analyte sensor 170, and/or the like. In some embodiments, drug delivery management application 140 may operate to perform profile adjustment processes according to some embodiments.

Controller 110 may be configured with a processor or processor circuitry 120, a memory unit 130, a user interface 182, a communication device or transceiver 180, and/or the like. Memory unit 130 may store information, such as patient information 132 and/or profile information 134, each of which may include previous analyte measurement values, delivered drug dosages, and/or the like.

In some embodiments, patient information 132 may include information associated with patient 150, including, without limitation, demographic information, physical information (for instance, height, weight, and/or the like), diabetes condition information (for instance, type of diagnosed diabetes (T1D or T2D)), insulin needs (for instance, MDI information, TDI information, insulin types, basal dosage information, bolus dosage information, and/or the like), activity information (for instance, meals and/or meal times, carbohydrate intake, exercise information, and/or the like), insulin sensitivity information, IOB information, response events, BG events (for example, hypoglycemic episodes or hyperglycemic episodes), and/or the like. In some embodiments, at least a portion of patient information 132 may be manually entered by patient 150 or a caregiver, for example, via a user interface of diabetes management application 140. In some embodiments, patient information 132 may include historical information, such as historical values associated with drug dosages, analyte measurement values (for instance, blood glucose measurements of patient 150), mealtimes, carbohydrate intake, exercise times, and/or the like. The historical information may include data from various time ranges, including at least seven days, at least 30 days, at least 60 days, at least the past 90 days, 180 days, 1 year, or more (and any range or value between any of these values, including endpoints). In some embodiments, profile information 134 may include a profile of patient 150 configured according to some embodiments. For example, profile information 134 may include a current patient correction factor and/or historical patient correction factors (including values and/or trends). Drug delivery management application 140 and/or an AAC (executing on controller 110 and/or drug delivery device 160) may use the correction factor to determine and deliver a dosage of the drug.

Additionally, memory unit 130 may store computer applications, such as a drug delivery management application 140, which may be or may include a medication delivery application (MDA), an automatic analyte control application, an AGC application, an analyte-based drug delivery application, an automatic analyte control application, an artificial pancreas application, an automated insulin delivery (AID) application, an automatic analyte control (AAC), and/or the like, that are executable by processor circuitry 120 and configure processor circuitry 120 to perform different functions according to some embodiments of the present disclosure. Drug delivery management application 140 may be or may include an "automatic analyte control application" that may refer to a computer application that is operable to execute an algorithm operable to use analyte measurement values, including blood glucose measurement values, to determine amounts of a drug to be delivered to a user.

Controller 110 when executing drug delivery management application 140 may be configured to set operational parameters for drug delivery device 160, such as user preferences for drug deliveries (e.g., times, basal and bolus) and notifications/alarms, drug delivery limits, user statistics (e.g., height, weight, gender, age, type of diabetes, or the like) as well as other settings.

Figure 8:
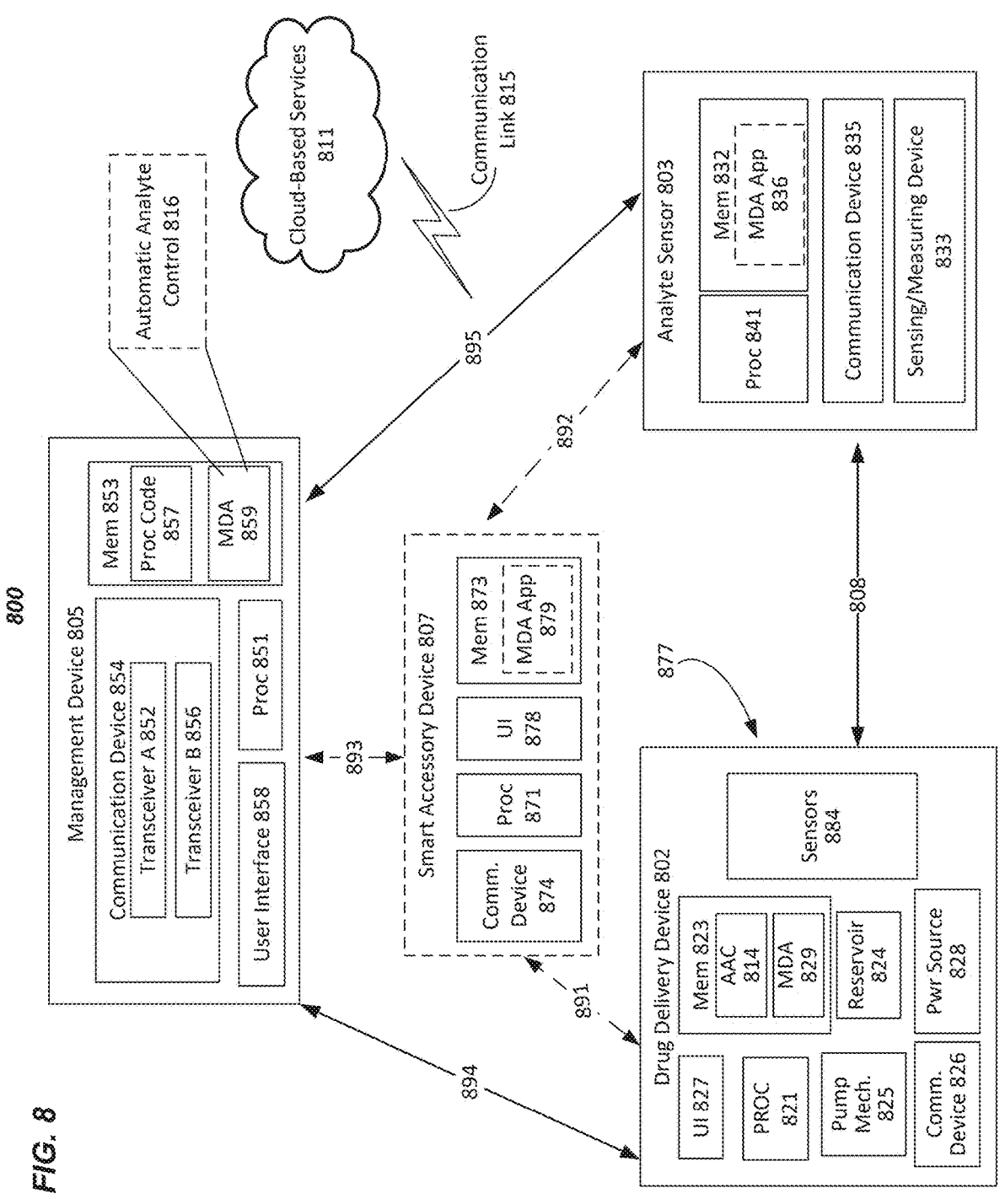
FIG. 8 illustrates a functional block diagram of a system in accordance with the present disclosure.

Drug delivery device 160 may also be configured with a processor, a memory, a user interface, a communication device, and/or other components (see, for example, FIG. 8). The memory may store information, such as previous analyte measurement values, delivered drug dosages, and the like. Additionally, the memory may store computer applications, such as a medication delivery application (MDA), automatic analyte control application 166, and the like, that are executable by the processor and configure drug delivery device 160 to perform different functions described in the present disclosure. Drug delivery device 160 may, during a drug delivery cycle, be configured to use the present analyte measurement value and information related to the present analyte measurement value to determine a dosage of a drug to be delivered during the cycle. The dosage of the drug may be a basal dosage, a bolus dosage (e.g., meal or correction), or a combination of both.

In some embodiments, a patient may be initialized or "onboarded" to a drug delivery device. For example, an AID application may be operable to, in response to an initial launch (i.e., first time the application is opened on a user device or used by a first-time (i.e., new) patient) or the request to begin the initial dose setting process, the AID application executing on a processor may, for example, set a default initial setting for determining total daily insulin (TDI) or dosage (TDD), a correction factor, and/or the like. The initial correction factor may be adjusted according to some embodiments as the patient uses the AID device to maintain blood glucose targets.

Figure 2:
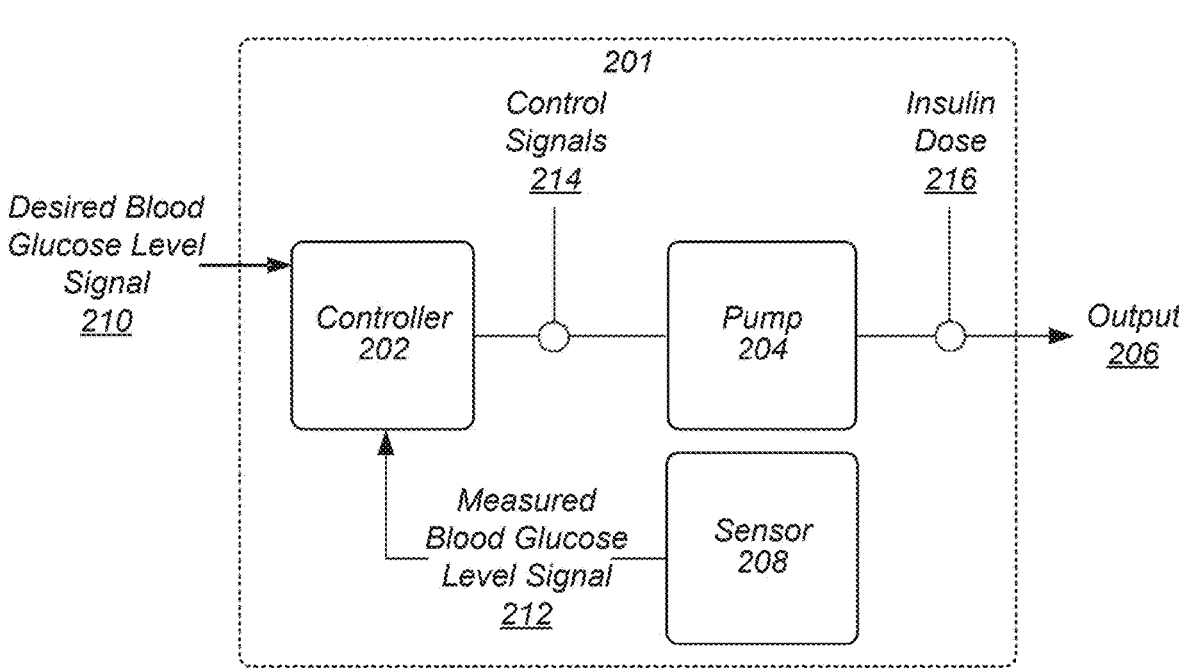
FIG. 2 illustrates a second exemplary embodiment of an operating environment in accordance with the present disclosure.

FIG. 2 illustrates a second exemplary embodiment of an operating environment in accordance with the present disclosure. As shown in FIG. 2, operating environment 200 may include an AID system 201 having a controller 202, a pump or other fluid extraction mechanism 204, and a sensor 208. The controller 202, pump 204, and sensor 208 may be communicatively coupled to one another via a wired or wireless communication path. For example, each of controller 202, pump 204 and sensor 208 may be equipped with a wireless radio frequency transceiver operable to communicate via one or more communication protocols, such as Wi-Fi, Bluetooth®, or the like. Sensor 208 may be a glucose monitor such as, for example, a CGM. In some embodiments, CGM 208 may, for example, be operable to measure blood glucose (BG) values of a user to generate a measured actual BG level signal 212.

As shown in the example, controller 202 may receive a desired BG level signal 210, which may be a first signal, indicating a desired blood BG level or range of a patient. Desired BG level signal 210 may be received from a user interface to the controller or other device, or by an algorithm that automatically determines a BG level for a patient. Sensor 208 may be coupled to the patient and may be operable to measure an approximate value of an actual BG level of the patient. The measured BG value, the actual BG level, the approximate measured value of the actual BG level may be approximate values of a patient's BG level In response to the measured BG level or value, sensor 208 may generate a signal indicating the measured BG value. As shown in the example of FIG. 2, controller 202 may also receive from sensor 208 via a communication path, a measured BG level signal 212, which may be a second signal, indicating an approximate measured value of the actual BG level of the user.

Based on desired BG level signal 210 and/or measured actual BG level signal 212, controller 202 may generate one or more control signals 214 for directing operation of pump 204. For example, control signal 214 may cause pump 204 to deliver a dose of insulin 216 to a patient via output 206. The dose of insulin 216 may, for example, be determined based on a difference between desired BG level signal 210 and actual BG signal level 212. The correction factor determined according to some embodiments may be used to determine the dosage as part of a closed loop control system implemented via an AID device (e.g., system 105, device 201, and/or the like). A dosage of insulin 216 may be determined as an appropriate amount of insulin to drive the actual BG level of the user to the desired BG level. Based on operation of pump 204 as determined by control signals 214, the patient may receive insulin 216 from pump 204. In various examples, one or more components of system 201 may be incorporated into a wearable or on body drug delivery system that is attached to the user.

Figure 3B:
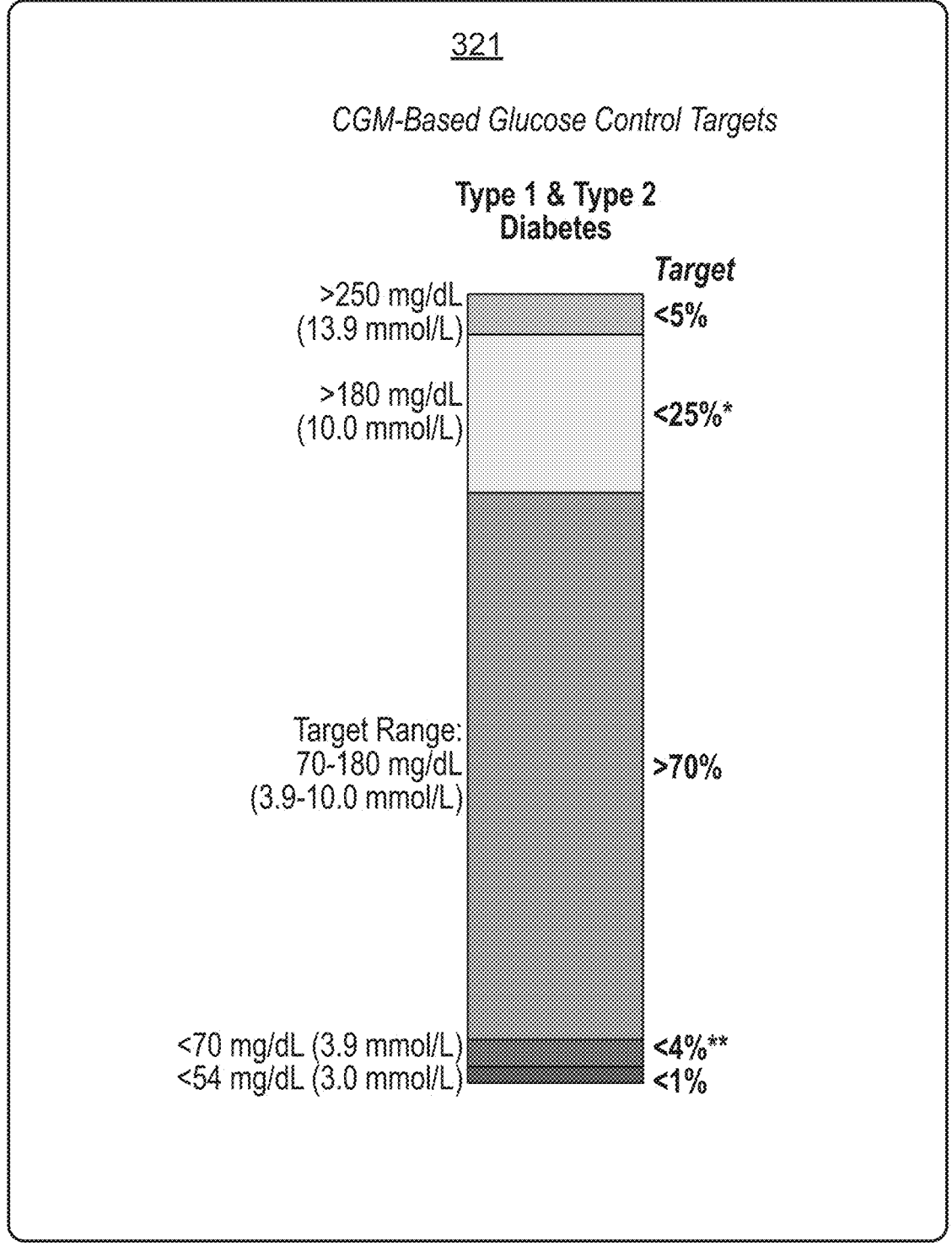

Automated medicament delivery devices may have certain control processes and algorithms determined based on certain standardized and/or industry metrics. FIGS. 3A and 3B illustrate examples of standardized glucose control metrics in accordance with the present disclosure for an AID device. More specifically, FIG. 3A depicts Standardized CGM Metrics for Clinical Care 301 and Target Guidance for Glycemic Control in T1D and T2D Patients 311 and FIG. 3B depicts CGM-Based Glucose Control Targets 321. CGM information 301, 311, and 321 are derived from Battelino et al, "Clinical Targets for Continuous Glucose Monitoring Data Interpretation: Recommendations From the International Consensus on Time in Range," Diabetes Care, 42(8), pp. 1593-1603 (2019) ("Clinical Targets for CGM"). As indicated in FIGS. 3A and 3B, patients are recommended to have at least 70% of their overall time using insulin delivery systems within the 70-180 mg/dL range, and a glucose variability of no more than 36%.

Based on the standardized glucose control metrics, the suitability of the current correction factor(s) for a patient may be estimated by reviewing the changes in the insulin-on-board (IOB) versus the total glucose excursion and meal ingestion records for the patient during a time period. A non-limiting example of a time period may be about 4 hours (for instance, how insulin was delivered in the last 4 hours). In various embodiments, the duration may be a duration of meal adsorption. In some embodiments, the time period may be about 5 minutes, about 10 minutes, about 15 minutes, about 30 minutes, about 1 hour, about 2 hours, about 3 hours, about 4 hours, about 5 hours, about 8 hours, about 12 hours, about 24 hours, about 48 hours, and any value or range between any two of these values (including endpoints).

In one example, based on a 4 hour time period (for instance, how insulin was delivered in the last 4 hours) insulin decay curve (see, for example, FIG. 4), the sum of all insulin that was delivered during the time period (the past 4 hours), minus the current IOB remaining may be determined as the total "insulin action" that was executed during the previous 4 hour time period for the patient according to the following Equation (1):

$$I_{action}(i) = \left(\sum\nolimits_{k=1}^{n} I(i-k)\right) - IOB(i).$$

The variable n may be determined based on (time period duration)/(duration increments). For example, for a duration of 4 hours with 5 minute increments, n=48. The duration and/or duration increments may be varied according to some embodiments to provide a different n value. In general, $I_{action}$ may be or may indicate the total insulin metabolized, for instance, as (injected insulin)–(remaining insulin).

Figure 4:
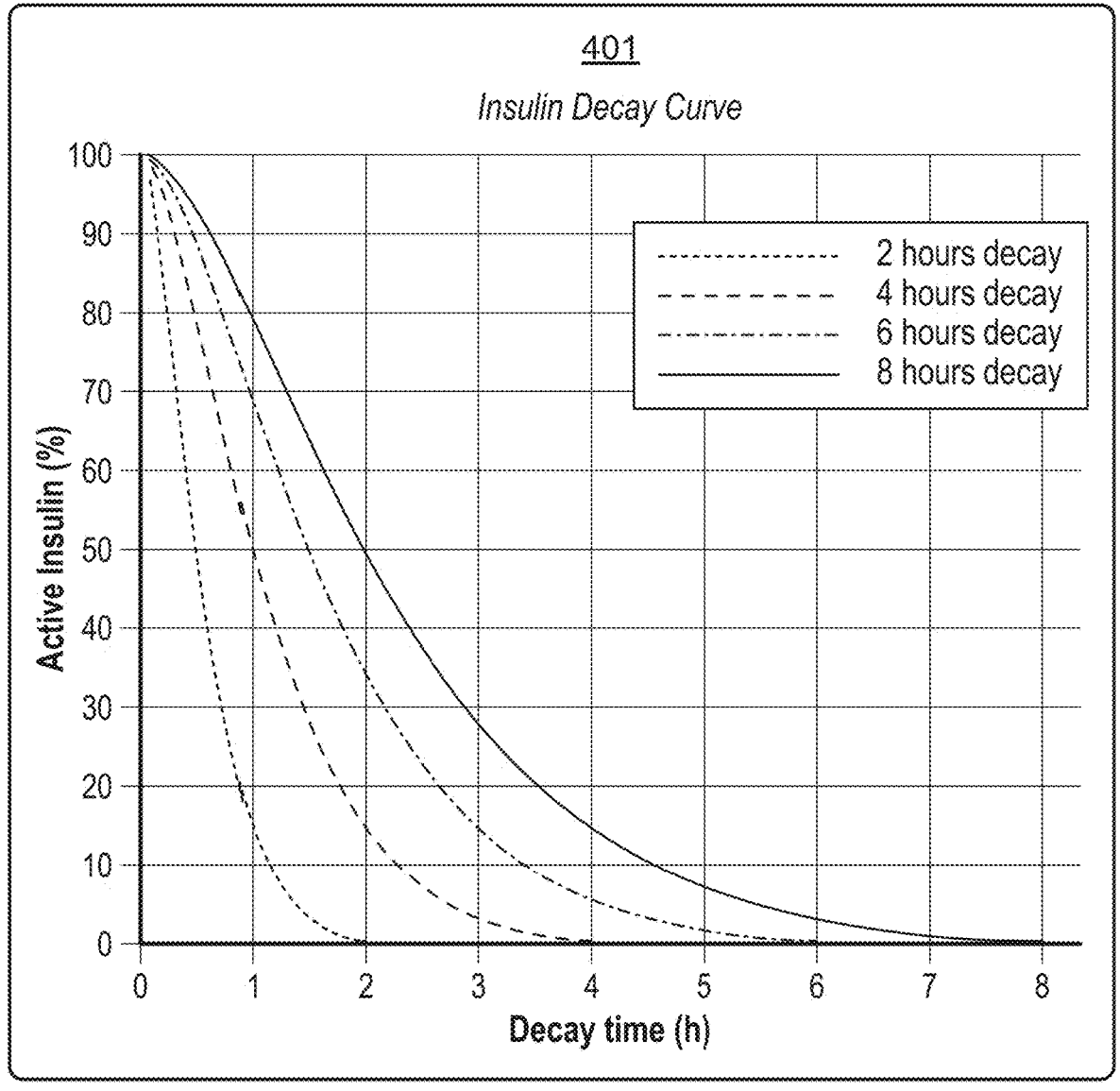
FIG. 4 illustrates an example insulin decay curve in accordance with the present disclosure.

FIG. 4 illustrates an example insulin decay curve in accordance with the present disclosure. As shown in FIG. 4, insulin decay information, such as presented in insulin decay curve 401 for various decay periods (for instance, 2 hours, 4 hours, 6 hours, and 8 hours), may be used to determine $I_{action}$ according to various embodiments. Insulin decay curve 401 provides a non-limiting example of insulin decay information. Additional and/or different insulin decay information may be used to determine values according to some embodiments. For example, the 4 hour decay curve may be used for rapid acting insulin.

In various embodiments, the correction factor determination process may determine glucose information over the duration. In some embodiments, the glucose information may include glucose activity, such as $G_{meal}$ and/or $G_{action}$.

In some embodiments, the relevant meal glucose action that may be calculated based on the meal ingestion during a meal absorption duration (for instance, in the last 4 hours, assuming a 4 hour meal absorption duration) versus the residual meal that is unabsorbed may be calculated based on one or more insulin-to-carb (IC) ratio rules for IC ratios (for instance, the 500 rule) and their conversion into glucose absorption (for instance, a sensitivity factor, such as the 1800 rule) according to the following Equations (2)-(4):

$$G_{meal}(i) = \left(\sum\nolimits_{k=1}^{48} CHO(i-k) - COB(i)\right) \cdot M_f,$$

$$COB(i) = \sum\nolimits_{k=1}^{48} (CHO(i-k) \cdot M_{abs}(k)), \text{ and}$$

$$M_f = \frac{\left(\frac{500}{TDI}\right)^{-1} \cdot 1800}{TDI} = \frac{1800}{500} = 3.6,$$

where $G_{meal}$ is the total carbohydrates metabolized (for instance, (carbohydrates ingested)–(carbohydrates remaining)), $M_{abs}$ is the estimated meal absorption curve characteristic, which may be estimated in a variety of methods, such as a linear estimation, $M_f$ is a meal factor (or excursion factor), CHO is all carbohydrates ingested. For Equation (4), different IC ratio rules and sensitivity factor rules other than 500 and 1800, respectively, may be used according to some embodiments. $M_f$ may be a value or indicator of how much a patient's glucose will increase, for example, glucose increase per gram of carbohydrate. The 3.6 $M_f$ value may represent the estimated change in glucose concentrations, for example, in mg/dL by ingestion of 1 g of carbohydrates. The $M_f$ value can vary depending on the range of heuristics that are utilized to calculate the correction factor and the insulin-to-carb ratio. For instance, the correction factor heuristic may utilize 1500 and the insulin-to-carb ratio heuristic may utilize 600, resulting in an $M_f$ value of 2.5. In another example, the correction factor heuristic may utilize 2000 and the insulin-to-carb ratio heuristic may utilize 400, resulting in an $M_f$ value of 5. There can be a wide range of such calculations.

In various embodiments, $G_{action}$ may be compared against a standard for clinical care (for example, Clinical Targets for CGM). In one example, $G_{action}$ may show a 36% margin against a glucose target of 125 (average) mg/dL, resulting in 170 (mean of target range) mg/dL, or other value of interest according to Equation (5):

$$G_{action}(i) = \frac{1}{48} \sum\nolimits_{k=1}^{48} (G(i-k) - 170).$$

In general, $G_{action}(i)$ may be or may include the real glucose excursion and $G(i-k)$ may be or may represent the measurement of glucose over the duration (for instance, 4 hours). The value 48 is derived from (4 hour duration)/(5 minute increments) and the value 170 is derived from applying a 36% margin against a target of 170 mg/dL. The 170 value may be a tunable target parameter, for example, where instead of assuming a 36% margin, a higher or lower margin of system action can be estimated, such as the typical changes in insulin needs and resulting target glucose concentrations by as much as 20% from the mean target glucose of 125 mg/dL, which is 144 mg/dL, or the threshold of hyperglycemia, which is 180 mg/dL, and/or other values.

In exemplary embodiments, the estimated correction factor ($CF_{est}$) during the duration may be determined by dividing $G_{action}$ (in the previous 4 hours or other duration) to the $I_{action}$ (in the previous 4 hours or other duration) as shown in the following Equation (6):

$$CF_{est}(i) = \frac{G_{action}(i) + G_{meal}(i)}{I_{action}(i)}.$$

In some embodiments, $G_{meal}$ may include uncompensated meals (for example, a sum of all of the ingested carbohydrates minus a sum of the absorbed carbohydrates (or glucose due to the uncompensated meals). In various embodiments, $G_{meal}$ may be excluded from Equation (6) such that $CF_{est}$ may be a determination of $G_{action}/I_{action}$ over a duration, such as the past 4 hours.

In various embodiments, $CF_{est}$ may be determined as a moving average with the user's mean estimated correction factor based on clinical heuristics of an insulin sensitivity factor (for instance, the 1800 rule) to provide the actual real-time estimate of correction factor according to the following Equation (7):

$$CF_{final}(i) = 0.8 \cdot \frac{1800}{\sum_{k=1}^{244} I(i-k)} + 0.2 \cdot CF_{est}(i).$$

The 0.8 and 0.2 terms represent the rate at which $CF_{final}$ is adapted to the $CF_{est}$ estimated parameter. The distributions of these terms may be modified, for example, to 0.95 and 0.05, or a 5% rate of adaptation, or to 0.75 and 0.25, or 25% rate of adaptation, or any values or ranges between 0 and 1, with the sum of both equal to 1.

Accordingly, in various embodiments, a correction factor determination process may operate to automatically determine a patient correction factor in real-time, substantially real-time, on-demand, expiry of a time period, and/or the like. The correction factor or correction factor estimate may be used to control a medication delivery device, such as an AID device, to deliver a dosage of a medication based on, among other things, the correction factor or correction factor estimate.

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 5:
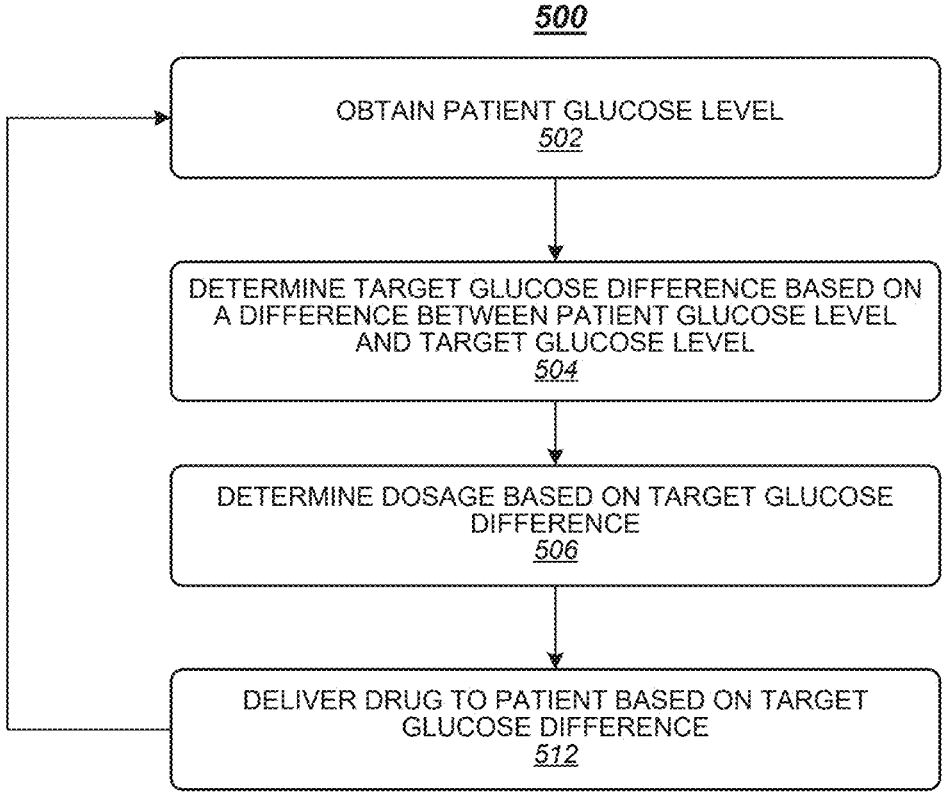
FIG. 5 illustrates a first logic flow in accordance with the present disclosure.

FIG. 5 illustrates an embodiment of a logic flow 500. Logic flow 400 may be representative of some or all of the operations executed by one or more embodiments described herein, such as devices of operating environment 100 and/or 800. For example, logic flow 500 may be performed by exemplary embodiments of an AID system in determining what dose of insulin to deliver to a patient as part of the closed loop control system.

At block 502, logic flow 500 may obtain a patient glucose level. In reference to FIG. 2, a BG level reading may be obtained by sensor 208. The BG level reading may be sent via a signal 212 to controller 202. At block 504, logic flow 500 may determine a target glucose difference based on a difference between the patient glucose level and the target glucose level. For example, controller 202 may calculate an error value as the difference between measured BG level 212 and desired BG level 210. Logic flow 500 may determine an insulin dosage based on the target glucose difference at block 506. In some embodiments, for example, the closed loop control system may attempt to minimize an aggregate penalty of a cost function over a wide range of possible dosages. The cost function may be applied to the possible dosages, and the dosage with the best penalty function value may be selected. At block 512, logic flow 500 may deliver the drug to the patient based on the target glucose difference. For example, control signal 214 may be generated by the controller 202 and sent to the pump 204 to cause the pump to deliver the desired insulin dose to the user.

Figure 6:
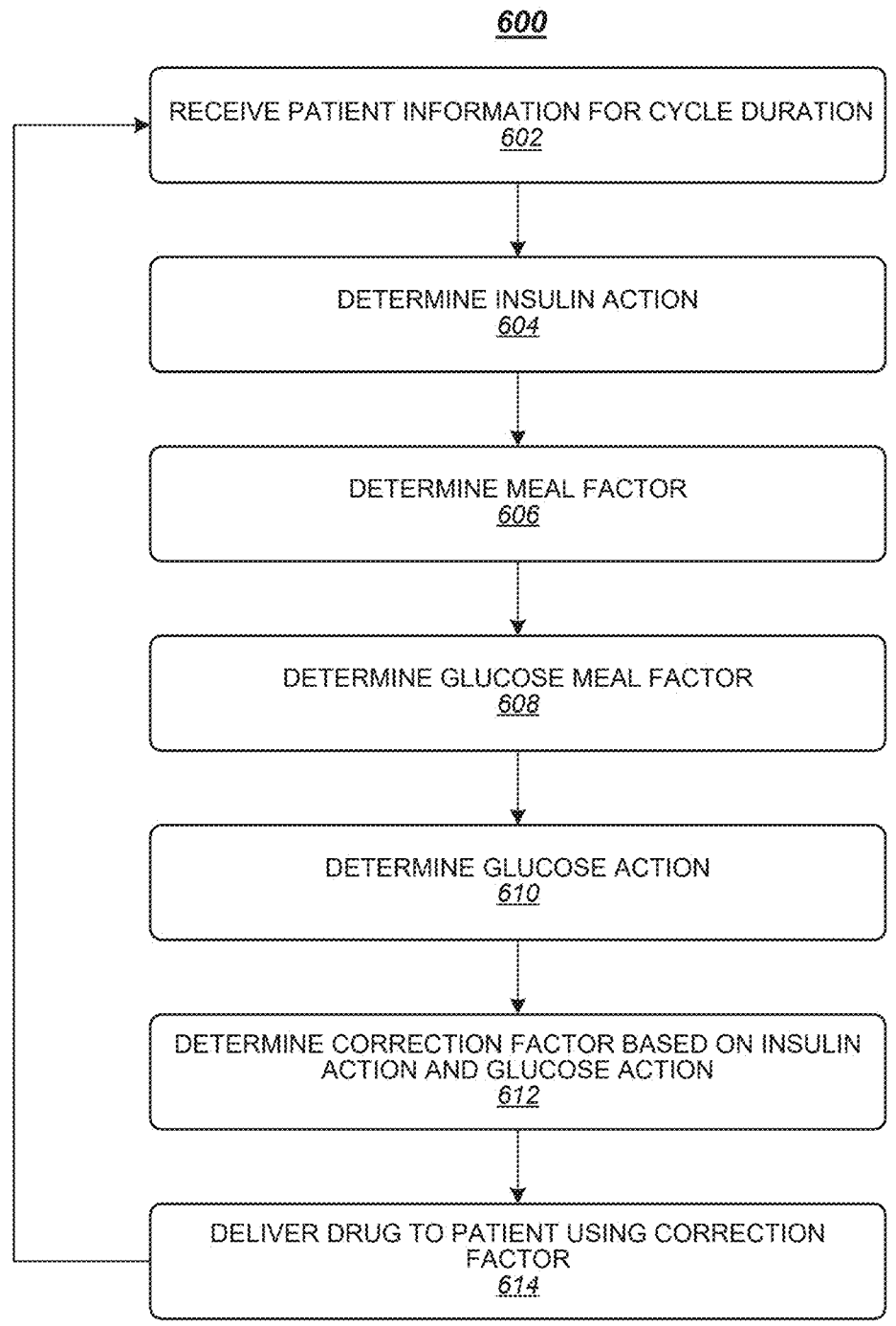
FIG. 6 illustrates a second logic flow in accordance with the present disclosure.

FIG. 6 illustrates an embodiment of a logic flow 600. Logic flow 600 may be representative of some or all of the operations executed by one or more embodiments described herein, such as devices of operating environment 100 and/or 800. For example, logic flow 600 may be or may include a correction factor determination process performed, for example, by controllers or other devices of operating environments 100, 200, and/or 800.

At block 602, logic flow 600 may receive patient information for a cycle duration. For example, a patient glucose level (for instance, BG) and meal (or carbohydrate) ingestion information may be determined may be determined for the cycle duration (for instance, 4 hours). The BG and/or carbohydrate information may be determined manually (for instance, via patient data entry) and/or automatically (for instance, via a CGM or automatic carbohydrate calculator based on meal information). Additional patient information may include, without limitation, TDI, TDD, and/or the like.

Logic flow 600 may determine an insulin action value at block 604. For example, logic flow 600 may determine $I_{action}$ according to the following Equation (1):

$$I_{action}(i) = \left( \sum_{k=1}^{n} I(i-k) \right) - IOB(i).$$

At block 606, logic flow 600 may determine a meal factor value. For example, logic flow 600 may determine $M_f$ according to the following Equation (4):

$$M_f = \frac{\left( \frac{500}{TDI} \right)^{-1} \cdot 1800}{TDI}.$$

At block 608, logic flow 600 may determine a glucose meal factor value. For example, logic flow 600 may determine according to the following Equation (2):

$$G_{meal}(i) = \left( \sum_{k=1}^{48} CHO(i-k) - COB(i) \right) \cdot M_f.$$

At block 610, logic flow 600 may determine a glucose action value. For example, logic flow 600 may determine $G_{action}$ according to the following Equation (5):

$$G_{action}(i) = \frac{1}{48}\sum_{k=1}^{48}(G(i-k)-170).$$

Logic flow may determine a correction factor value based on the insulin action and the glucose action at block 612. For example, logic flow 600 may determine $CF_{est}$ according to the following Equation (6):

$$CF_{est}(i) = \frac{G_{action}(i) + G_{meal}(i)}{I_{action}(i)}.$$

At block 612, logic flow may deliver the drug to the patient using the correction factor. For example, control signal 214 may be generated by the controller 202 and sent to the pump 204 to cause the pump to deliver the desired insulin dose to the user. For instance, the resulting $CF_{est}$ utilized by the user may be calculated as 40, indicating that 1 U of insulin will reduce the user's glucose concentration by 40 mg/dL. Then, if the control signal requires the user's glucose concentration to be reduced by 60 mg/dL, the system would deliver 60 divided by 40, or 1.5 U of insulin.

Figure 7:
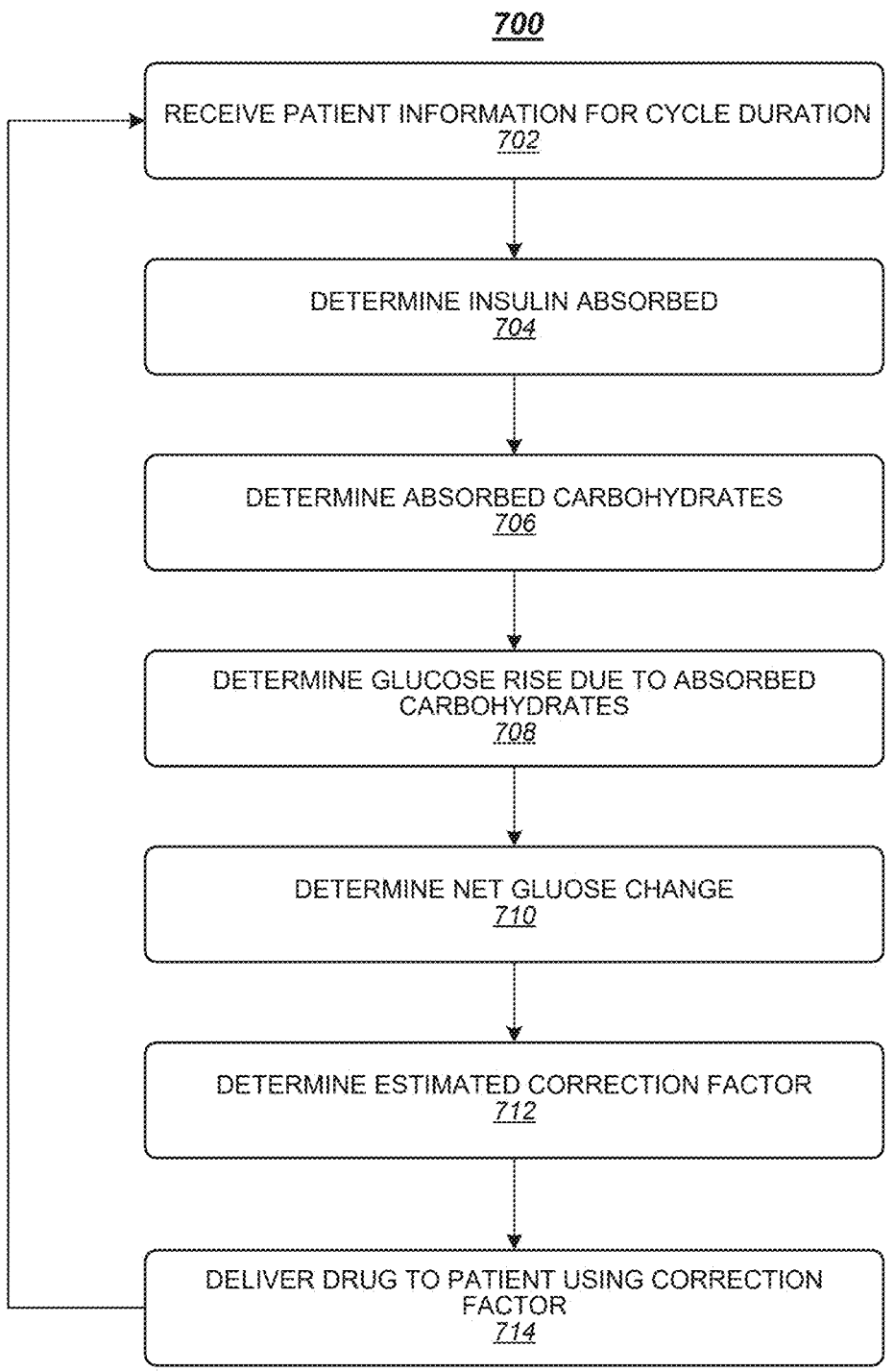
FIG. 7 illustrates a third logic flow in accordance with the present disclosure.

FIG. 7 illustrates an embodiment of a logic flow 700. Logic flow 700 may be representative of some or all of the operations executed by one or more embodiments described herein, such as devices of operating environment 100 and/or 800. For example, logic flow 600 may be a correction factor determination process based on meal ingestion and meal insulin bolus performed, for example, by controllers or other devices of operating environments 100, 200, and/or 800.

At block 702, logic flow 700 may receive patient information for a cycle duration. Non-limiting examples of patient information may include BG levels, meal (or carbohydrate) ingestion information, TDI, TDD, and/or the like. The patient information may be determined at specified increments (for instance, every 5 minutes), an average, a mean, and/or the like.

Logic flow 700 may determine insulin absorbed at block 704. For example, insulin absorbed may equal (insulin injected)—IOB. At block 706, logic flow 700 may determine absorbed carbohydrates. For example, absorbed carbohydrates may equal (carbohydrates ingested)—COB. At block 708, logic flow 700 may determine a glucose rise due to absorbed carbohydrates, for example, an estimated or projected glucose rise due to absorbed carbohydrates. Logic flow 700 may determine a net glucose change at block 710. The net glucose change may be an excursion, such as a rise or drop. At block 712, logic flow 700 may determine an estimated correction factor. For example, the estimated correction factor may equal (net glucose change+projected glucose rise)/absorbed insulin. Logic flow 700 my deliver a drug to the patient using the correction factor at block 714.

FIG. 8 illustrates a functional block diagram of a system example suitable for implementing the example processes and techniques described herein.

The operating environment 800 may be or may include an automatic drug delivery system that may include components such as an automatic drug delivery system that is configured to determine a drug dosage and deliver the dosage of the drug without any user interaction, or in some examples, limited user interaction, such as in response to a user depressing a button to indicate measurement of blood glucose or another analyte, or the like. "Drug delivery system environment" may refer to a computing and sensing environment that includes cloud based services, a drug delivery system (that may include a controller, a drug delivery device, and an analyte sensor) and optionally additional devices. The components of the drug delivery system environment may cooperate to provide present analyte measurement values or at least accurate estimates of present analyte measurement values to facilitate calculation of optimal drug dosages for a user.

The automatic drug delivery system 800 may implement (and/or provide functionality for) a medication delivery algorithm, such as an artificial pancreas (AP) application, to govern or control automated delivery of a drug or medication, such as insulin, to a user (e.g., to maintain euglycemia—a normal level of glucose in the blood). The drug delivery system 800 may be an automated drug delivery system that may include a wearable automatic drug delivery device 802, an analyte sensor 803, and a management device (for instance, a PDM, smart phone, table computing device, and/or the like) 805.

The system 800, in an optional example, may also include a smart accessory device 807, such as a smartwatch, a personal assistant device or the like, which may communicate with the other components of system 800 via either a wired or wireless communication links 891-893.

The management device or controller 805 may be a computing device such as a smart phone, a tablet, a personal diabetes management device, a dedicated diabetes therapy management device, or the like. In an example, the management device 805 may include a processor 851, a management device memory 853, a user interface 858, and a communication device 854. The management device 805 may contain analog and/or digital circuitry that may be implemented as a processor 851 for executing processes based on programming code stored in the management device memory 853, such as the medication delivery algorithm or application (MDA) 859, to manage a user's blood glucose levels and for controlling the delivery of the drug, medication, or therapeutic agent to the user as well as other functions, such as calculating carbohydrate-compensation dosage, a correction bolus dosage and the like as discussed above. The management device 805 may be used to program, adjust settings, and/or control operation of the wearable automatic drug delivery device 802 and/or the analyte sensor 803 as well as the optional smart accessory device 807.

The processor 851 may also be configured to execute programming code stored in the management device memory 853, such as the MDA 859. The MDA 859 may be a computer application that is operable to deliver a drug based on information received from the analyte sensor 803, the cloud-based services 811 and/or the management device 805 or optional smart accessory device 807. The memory 853 may also store programming code to, for example, operate the user interface 858 (e.g., a touchscreen device, a camera or the like), the communication device 854 and the like. The processor 851 when executing the MDA 859 may be configured to implement indications and notifications related to meal ingestion, blood glucose measurements, and the like. The user interface 858 may be under the control of the processor 851 and be configured to present a graphical user interface that enables the input of a meal announcement, adjust setting selections and the like as described above.

In a specific example, when the MDA 859 is an artificial pancreas (AP) application, the processor 851 is also configured to execute a diabetes treatment plan (which may be stored in a memory) that is managed by the MDA 859 stored in memory 853. In addition to the functions mentioned above, when the MDA 859 is an AP application, it may further provide functionality to enable the processor 851 to determine a carbohydrate-compensation dosage, a correction bolus dosage and determine a basal dosage according to a diabetes treatment plan. In addition, as an AP application, the MDA 859 provides functionality to enable the processor 851 to output signals to the wearable automatic drug delivery device 802 to deliver the determined bolus and basal dosages described with reference to the examples of FIGS. 1-4.

The communication device 854 may include one or more transceivers such as Transceiver A 852 and Transceiver B 856 and receivers or transmitters that operate according to one or more radio-frequency protocols. In the example, the transceivers 852 and 856 may be a cellular transceiver and a Bluetooth® transceiver, respectively. For example, the communication device 854 may include a transceiver 852 or 856 configured to receive and transmit signals containing information usable by the MDA 859.

The wearable automatic drug delivery device 802, in the example system 800, may include a user interface 827, a controller 821, a drive mechanism 825, a communication device 826, a memory 823, a power source/energy harvesting circuit 828, device sensors 884, and a reservoir 824. The wearable automatic drug delivery device 802 may be configured to perform and execute the processes described in the examples of FIGS. 4, 5, and 7 without input from the management device 805 or the optional smart accessory device 807. As explained in more detail, the controller 821 may be operable, for example, implement the processes of FIGS. 4, 5, and 7 as well as determine an amount of insulin delivered, IOB, insulin remaining, and the like. The controller 821 alone may implement the processes of FIGS. 4, 5, and 7 as well as determine an amount of insulin delivered, IOB, insulin remaining, and the like, such as control insulin delivery, based on an input from the analyte sensor 804.

The memory 823 may store programming code executable by the controller 821. The programming code, for example, may enable the controller 821 to control expelling insulin from the reservoir 824 and control the administering of doses of medication based on signals from the MDA 829 or, external devices, if the MDA 829 is configured to implement the external control signals.

The reservoir 824 may be configured to store drugs, medications or therapeutic agents suitable for automated delivery, such as insulin, morphine, blood pressure medicines, chemotherapy drugs, or the like.

The device sensors 884 may include one or more of a pressure sensor, a power sensor, or the like that are communicatively coupled to the controller 821 and provide various signals. For example, the pressure sensor may be coupled to or integral with a needle/cannula insertion component (which may be part of the drive mechanism 825) or the like. In an example, the controller 821 or a processor, such as 851, may be operable to determine that a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount.

In an example, the wearable automatic drug delivery device 802 includes a communication device 826, which may be a receiver, a transmitter, or a transceiver that operates according to one or more radio-frequency protocols, such as Bluetooth, Wi-Fi, a near-field communication standard, a cellular standard, or the like. The controller 821 may, for example, communicate with a personal diabetes management device 805 and an analyte sensor 803 via the communication device 826.

The wearable automatic drug delivery device 802 may be attached to the body of a user, such as a patient or diabetic, at an attachment location and may deliver any therapeutic agent, including any drug or medicine, such as insulin or the like, to a user at or around the attachment location. A surface of the wearable automatic drug delivery device 802 may include an adhesive to facilitate attachment to the skin of a user as described in earlier examples.

The wearable automatic drug delivery device 802 may, for example, include at least one housing, a reservoir 824 for storing the drug (such as insulin), a needle or cannula (not shown in this example) for delivering the drug into the body of the user (which may be done subcutaneously, intraperitoneally, or intravenously), and a drive mechanism 825 for transferring the drug from the reservoir 824 through a needle or cannula and into the user. The drive mechanism 825 may be fluidly coupled to reservoir 824, and communicatively coupled to the controller 821.

The wearable automatic drug delivery device 802 may further include a power source 828, such as a battery, a piezoelectric device, other forms of energy harvesting devices, or the like, for supplying electrical power to the drive mechanism 825 and/or other components (such as the controller 821, memory 823, and the communication device 826) of the wearable automatic drug delivery device 802.

In some examples, the wearable automatic drug delivery device 802 and/or the management device 805 may include a user interface 858, respectively, such as a keypad, a touchscreen display, levers, light-emitting diodes, buttons on a housing of the management device 805, a microphone, a camera, a speaker, a display, or the like, that is configured to allow a user to enter information and allow the management device 805 to output information for presentation to the user (e.g., alarm signals or the like). The user interface 858 may provide inputs, such as a voice input, a gesture (e.g., hand or facial) input to a camera, swipes to a touchscreen, or the like, to processor 851 which the programming code interprets.

When configured to communicate to an external device, such as the PDM 805 or the analyte sensor 804, the wearable automatic drug delivery device 802 may receive signals over the wired or wireless link 894 from the management device (PDM) 805 or 808 from the analyte sensor 804. The controller 821 of the wearable automatic drug delivery device 802 may receive and process the signals from the respective external devices as well as implementing delivery of a drug to the user according to a diabetes treatment plan or other drug delivery regimen.

In an operational example, the processor 821 when executing the MDA 859 may output a control signal operable to actuate the drive mechanism 825 to deliver a dosage of insulin based on a correction factor determined according to some embodiments.

The smart accessory device 807 may be, for example, an Apple Watch®, other wearable smart device, including eyeglasses, provided by other manufacturers, a global positioning system-enabled wearable, a wearable fitness device, smart clothing, or the like. Similar to the management device 805, the smart accessory device 807 may also be configured to perform various functions including controlling the wearable automatic drug delivery device 802. For example, the smart accessory device 807 may include a communication device 874, a processor 871, a user interface 878 and a memory 873. The user interface 878 may be a graphical user interface presented on a touchscreen display of the smart accessory device 807. The memory 873 may store programming code to operate different functions of the smart accessory device 807 as well as an instance of the MDA 879. The processor 871 that may execute programming code, such as site MDA 879 for controlling the wearable automatic drug delivery device 802 to processes described herein.

The analyte sensor 803 may include a controller 831, a memory 832, a sensing/measuring device 833, a user interface 837, a power source/energy harvesting circuitry 834, and a communication device 835. The analyte sensor 803 may be communicatively coupled to the processor 851 of the management device 805 or controller 821 of the wearable automatic drug delivery device 802. The memory 832 may be configured to store information and programming code, such as an instance of the MDA 836.

The analyte sensor 803 may be configured to detect multiple different analytes, such as lactate, ketones, uric acid, sodium, potassium, alcohol levels or the like, and output results of the detections, such as measurement values or the like. The analyte sensor 803 may, in an example, be configured to measure a blood glucose value at a predetermined time interval, such as every 30 seconds, every 1 minute, every 5 minutes, every 10 minutes, every 30 minutes, every hour, every cycle, and/or other time intervals. The communication device 835 of analyte sensor 803 may have circuitry that operates as a transceiver for communicating the measured blood glucose values to the management device 805 over a wireless link 895 or with wearable automatic drug delivery device 802 over the wireless communication link 808. While called an analyte sensor 803, the sensing/measuring device 833 of the analyte sensor 803 may include one or more additional sensing elements, such as a glucose measurement element a heart rate monitor, a pressure sensor, or the like. The controller 831 may include discrete, specialized logic and/or components, an application-specific integrated circuit, a microcontroller or processor that executes software instructions, firmware, programming instructions stored in memory (such as memory 832), or any combination thereof.

Similar to the controller 821, the controller 831 of the analyte sensor 803 may be operable to perform many functions. For example, the controller 831 may be configured by the programming code stored in the memory 832 to manage the collection and analysis of data detected the sensing and measuring device 833.

Although the analyte sensor 803 is depicted in FIG. 8 as separate from the wearable automatic drug delivery device 802, in various examples, the analyte sensor 803 and wearable automatic drug delivery device 802 may be incorporated into the same unit. That is, in various examples, the sensor 803 may be a part of the wearable automatic drug delivery device 802 and contained within the same housing of the wearable automatic drug delivery device 802 (e.g., the sensor 803 or, only the sensing/measuring device 833 and memory storing related programming code may be positioned within or integrated into, or into one or more components, such as the memory 823, of, the wearable automatic drug delivery device 802). In such an example configuration, the controller 821 may be able to implement processes alone without any external inputs from the management device 805, the cloud-based services 811, another sensor (not shown), the optional smart accessory device 807, or the like.

The communication link 815 that couples the cloud-based services 811 to the respective devices 802, 803, 805 or 807 of system 800 may be a cellular link, a Wi-Fi link, a Bluetooth link, or a combination thereof. Services provided by cloud-based services 811 may include data storage that stores anonymized data, such as blood glucose measurement values, historical IOB or TDI, prior carbohydrate-compensation dosage, and other forms of data. In addition, the cloud-based services 811 may process the anonymized data from multiple users to provide generalized information related to TDI, insulin sensitivity, IOB and the like.

The wireless communication links 808, 891, 892, 893, 894 and 895 may be any type of wireless link operating using known wireless communication standards or proprietary standards. As an example, the wireless communication links 808, 891, 892, 893, 894 and 895 may provide communication links based on Bluetooth®, Zigbee®, Wi-Fi, a near-field communication standard, a cellular standard, or any other wireless protocol via the respective communication devices 854, 874, 826 and 835.

Software related implementations of the techniques described herein, such as the processes examples described with reference to FIGS. 5-7 may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed AP application and algorithms may be operable to perform various functions related to open loop operations, such as the generation of prompts requesting the input of information such as weight or age. Similarly, a dosage amount of insulin may be received by the AP application or algorithm from a user via a user interface. Other open-loop actions may also be implemented by adjusting user settings or the like in an AP application or algorithm.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

The invention claimed is:

1. A controller for operating an insulin delivery device, comprising:

a processor; and a memory storing instructions that, when executed by the processor, operate the controller to:

determine an insulin action ($I_{action}$) for a patient over a duration, the insulin action representing a total insulin metabolized;

determine glucose information for the patient over the duration, the glucose information representing glucose activity, wherein the glucose activity is calculated based on the meal ingestion during the duration versus the residual meal that is unabsorbed; and determine an estimated correction factor ($CF_{est}$) based on (glucose information)/(insulin action) for the duration, wherein the estimated correction factor is used by the insulin delivery device to deliver an amount of insulin.

2. The controller of claim 1, the $I_{action}$ determined based on an insulin decay curve for the duration.

3. The controller of claim 2, the $I_{action}$ determined using the following:

$$I_{action}(i) = \left(\sum_{k=1}^{n} I(i-k)\right) - IOB(i),$$

where n is determined based on (duration)/(duration increments).

4. The controller of claim 1, the glucose information comprising a glucose action ($G_{action}$) value.

5. The controller of claim 4, the $G_{action}$ determined using the following:

$$G_{action}(i) = \frac{1}{48}\sum_{k=1}^{48} (G(i-k)-x),$$

where x is a target glucose value.

6. The controller of claim 4, the glucose information comprising a glucose meal excursion value ($G_{meal}$).

7. The controller of claim 6, the Great value determined using the following:

$$G_{meal}(i) = \left(\sum_{k=1}^{48} CHO(i-k) - COB(i)\right) \cdot M_f,$$

where CHO is all carbohydrates ingested, COB is carbohydrates-on-board, and $M_f$ is a meal factor.

8. The controller of claim 1, the instructions, when executed by the processor, to operate the controller to determine a final correction factor ($CF_{final}$) based on $CF_{est}$ using the following:

$$CF_{final}(i) = 0.8 \cdot \frac{1800}{\sum_{k=1}^{244} I(i-k)} + 0.2 \cdot CF_{est}(i).$$

9. The controller of claim 1, the duration comprising about 4 hours.

10. A method for operating a drug delivery device, comprising, via a processor of a controller:

determining an insulin action ($I_{action}$) for a patient over a duration, the insulin action representing a total insulin metabolized;

determining glucose information for the patient over the duration, the glucose information representing glucose activity, wherein the glucose activity is calculated based on the meal ingestion during the duration versus the residual meal that is unabsorbed; and determining an estimated correction factor ($CF_{est}$) based on (glucose information)/(insulin action) for the duration, wherein the estimated correction factor is used by the insulin delivery device to deliver an amount of insulin.

11. The method of claim 10, the $I_{action}$ determined based on an insulin decay curve for the duration.

12. The method of claim 11, the $I_{action}$ determined using the following:

$$I_{action}(i) = \left( \sum_{k=1}^{n} I(i-k) \right) - IOB(i),$$

where n is determined based on (duration)/(duration increments).

13. The method of claim 12, the glucose information comprising a glucose action ($G_{action}$) value.

14. The method of claim 13, the $G_{action}$ determined using the following:

$$G_{action}(i) = \frac{1}{48} \sum_{k=1}^{48} (G(i-k) - x),$$

where x is a target glucose value.

15. The method of claim 13, the glucose information comprising a glucose meal excursion value ($G_{meal}$).

16. The method of claim 15, the $G_{meal}$ value determined using the following:

$$G_{meal}(i) = \left( \sum_{k=1}^{48} CHO(i-k) - COB(i) \right) \cdot M_f,$$

where CHO is all carbohydrates ingested, COB is carbohydrates-on-board, and $M_f$ is a meal factor.

17. The method of claim 10, comprising determining a final correction factor ($CF_{final}$) based on $CF_{est}$ using the following:

$$CF_{final}(i) = 0.8 \cdot \frac{1800}{\sum_{k=1}^{244} I(i-k)} + 0.2 \cdot CF_{est}(i).$$

18. The method of claim 10, the duration comprising about 4 hours.

* * * * *